(12) United States Patent
Pereira et al.

(10) Patent No.: US 10,543,072 B2
(45) Date of Patent: Jan. 28, 2020

(54) IMPLANT FIXATION DEVICES AND METHODS OF USING THE SAME

(71) Applicant: Boston Scientific Scimed, Inc., Maple Grove, MN (US)

(72) Inventors: Peter J. Pereira, Mendon, MA (US); Aaron Kirkemo, Gladstone, NJ (US); James M. Goddard, Pepperell, MA (US); Shane Siwinski, Providence, RI (US); Ayan A. Bhandari, Roanoke, VA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 38 days.

(21) Appl. No.: 15/272,674

(22) Filed: Sep. 22, 2016

(65) Prior Publication Data
US 2017/0086882 A1    Mar. 30, 2017

Related U.S. Application Data

(60) Provisional application No. 62/232,029, filed on Sep. 24, 2015.

(51) Int. Cl.
| | |
|---|---|
| *A61F 2/00* | (2006.01) |
| *A61B 17/04* | (2006.01) |
| *A61B 17/064* | (2006.01) |
| *A61B 17/06* | (2006.01) |
| *A61B 17/00* | (2006.01) |
| *A61B 17/068* | (2006.01) |

(52) U.S. Cl.
CPC ........ *A61F 2/0022* (2013.01); *A61B 17/0401* (2013.01); *A61B 17/064* (2013.01); *A61F 2/0045* (2013.01); *A61B 17/068* (2013.01); *A61B 2017/00805* (2013.01); *A61B 2017/0409* (2013.01); *A61B 2017/0417* (2013.01); *A61B 2017/0419* (2013.01); *A61B 2017/0464* (2013.01); *A61B 2017/06042* (2013.01); *A61B 2017/0647* (2013.01); *A61B 2017/06176* (2013.01)

(58) Field of Classification Search
CPC ............ A61B 17/0487; A61B 17/0401; A61B 2017/0409; A61B 2017/0488; A61B 2017/3488; A61B 2017/00349
See application file for complete search history.

(56) References Cited

U.S. PATENT DOCUMENTS

| | | | | |
|---|---|---|---|---|
| 5,392,978 | A | * | 2/1995 | Velez ................ A61B 17/0644 227/175.1 |
| 5,653,373 | A | * | 8/1997 | Green ............. A61B 17/07207 227/175.1 |

(Continued)

FOREIGN PATENT DOCUMENTS

WO    WO 2015128835 A1 *   9/2015   ......... A61B 17/0401

*Primary Examiner* — Kaylee R Wilson
(74) *Attorney, Agent, or Firm* — Brake Hughes Bellermann LLP (57) ABSTRACT

According to an aspect, a medical device includes an elongate member, a first arm extending from the elongate member, a second arm extending from the elongate member, the second arm being configured to move with respect to the first arm, and a needle coupled to the elongate member, the needle being configured to move with respect to the elongate member.

20 Claims, 8 Drawing Sheets

(56) References Cited

U.S. PATENT DOCUMENTS

| | | | | |
|---|---|---|---|---|
| 2002/0116010 A1* | 8/2002 | Chung | ............... | A61B 17/0469 606/139 |
| 2002/0147456 A1* | 10/2002 | Diduch | .............. | A61B 17/0469 606/144 |
| 2009/0093824 A1* | 4/2009 | Hasan | ................ | A61B 17/0401 606/139 |
| 2010/0249814 A1* | 9/2010 | Vaughan | ............ | A61B 17/0401 606/153 |

* cited by examiner

IMPLANT FIXATION DEVICES AND METHODS OF USING THE SAME

CROSS-REFERENCE TO RELATED APPLICATION

This application is a Nonprovisional of, and claims priority to, U.S. Patent Application No. 62/232,029, filed on Sep. 24, 2015, entitled "IMPLANT FIXATION DEVICES AND METHODS OF USING THE SAME", which is incorporated by reference herein in its entirety.

TECHNICAL FIELD

This disclosure relates generally to medical devices and more particularly to medical devices that are configured to place or couple bodily implants within a body of a patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures have included placing implants within the pelvic region of the patient. Some of the implants are delivered to the pelvic region of the patient through one or more vaginal incisions, and/or through exterior incisions in the patient.

Often such implants are delivered or placed within the body of the patient and coupled or attached to various locations within the body using a series of sutures or knots. For example, in procedures such as sacrocolpopexy procedures, a suture may be tied 4 to 8 times to form a single knot and a series of 12 of more knots may be used to secure an implant within the body of the patient. Accordingly, a procedure for placing and attaching an implant within a body of a patient may require time and skill.

Accordingly, it may be desirable to provide a delivery or coupling tool that includes components or features that would facilitate the delivery and/or attachment process of implants within a body of a patient.

SUMMARY

According to an aspect, a medical device includes an elongate member, a first arm extending from the elongate member, a second arm extending from the elongate member, the second arm being configured to move with respect to the first arm, and a needle coupled to the elongate member, the needle being configured to move with respect to the elongate member.

In some embodiments, the first arm is configured to move with respect to the second arm. In some embodiments, the medical device includes an actuation mechanism configured to cause the second arm to move with respect to the first arm in response to being actuated. In some embodiments, the medical device includes an actuation mechanism configured to cause the needle to move with respect to the elongate member in response to being actuated. In some embodiments, the medical device includes a first actuation mechanism configured to cause the second arm to move with respect to the first arm in response to being actuated, and a second actuation mechanism configured to cause the needle to move with respect to the elongate member in response to being actuated.

In some embodiments, the elongate member defines a lumen, the lumen is configured to retain a plurality of tissue anchors.

In some embodiments, the needle includes a curved portion. In some embodiments, the needle includes a curved portion and is rotatably coupled to the elongate member.

In some embodiments, the first arm includes a non-planar surface, the non-planar surface is configured to contact at least one of a bodily implant and bodily tissue of a patient. In some embodiments, the first arm includes a non-planar surface, the non-planar surface of the first arm is configured to contact at least one of a bodily implant and bodily tissue of a patient, the second arm includes a non-planar surface, the non-planar surface of the second arm is configured to contact at least one of a bodily implant and bodily tissue of the patient.

In some embodiments, the second arm is rotatably coupled to the elongate member. In some embodiments, the second arm is pivotally coupled to the elongate member. In some embodiments, the first arm is rotatably coupled to the elongate member. In some embodiments, the first arm is pivotally coupled to the elongate member.

In some embodiments, the needle is configured to rotate about a first axis, the elongate member defines a longitudinal axis, and the first axis is substantially perpendicular to the longitudinal axis.

In some aspects a medical device includes an elongate member, a first arm extending from the elongate member, the first arm being configured to move with respect to the elongate member, a second arm extending from the elongate member, the second arm being configured to move with respect to the elongate member, and a needle coupled to the elongate member, the needle being configured to move with respect to the elongate member.

In some embodiments, the first arm is pivotally coupled to the elongate member. In some embodiments, the first arm is rotatably coupled to the elongate member. In some embodiments, the medical device includes an actuation mechanism configured to cause the second arm to move with respect to the first arm in response to being actuated. In some embodiments, the medical device includes an actuation mechanism configured to cause the needle to move with respect to the elongate member in response to being actuated. In some embodiments, the medical device includes a first actuation mechanism configured to cause the second arm to move with respect to the first arm in response to being actuated, and a second actuation mechanism configured to cause the needle to move with respect to the elongate member in response to being actuated.

In some embodiments, the elongate member defines a lumen, the lumen is configured to retain a plurality of tissue anchors.

In some aspects a method includes inserting a medical device into a body of a patient, the medical device, including an elongate member, a first arm extending from the elongate member, a second arm extending from the elongate member, the second arm being configured to move with respect to the first arm, and a needle coupled to the elongate member, the needle being configured to move with respect to the elongate member; actuating a first actuation member to move the second arm with respect to the first arm to disposed a portion of a bodily implant and bodily tissue of a patient between the first arm and the second arm; and actuating a second actuation member to move the needle with respect to the elongate member and insert an anchor into the bodily implant and the bodily tissue.

In some embodiments, the elongate member defines a lumen, the lumen retains the anchor during the inserting. In some embodiments, the needle includes a curved portion and is configured to rotate with respect to the elongate member in response to the actuating of the second actuation member.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1:
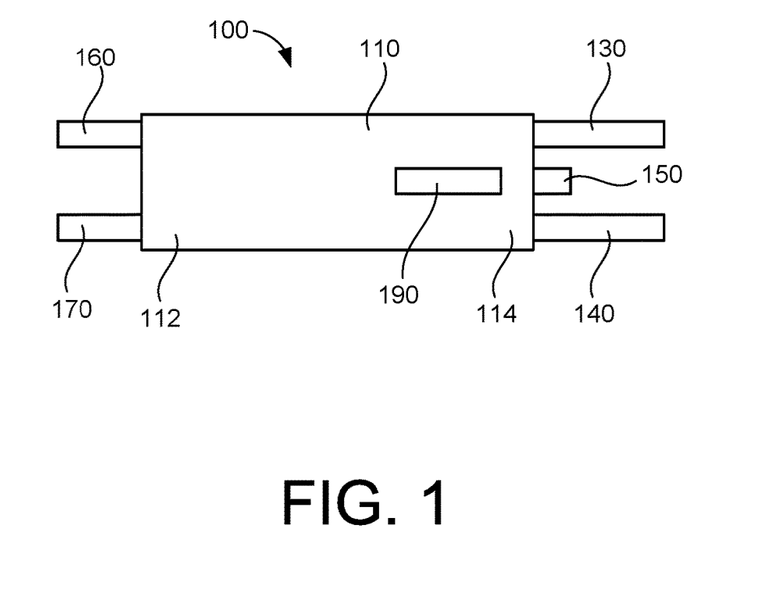
FIG. 1 is a schematic illustration of a medical device according to an embodiment.

FIG. 1 is a schematic illustration of a medical device 100 according to an embodiment of the invention. The medical device 100 may be used to couple or attach a bodily implant within a body of a patient. For example, the medical device 100 may be used to couple or attach an implant within a pelvic region of a patient. For example, in some embodiments, the medical device 100 may be used in a sacrocolpopexy procedure to couple an implant to a vagina or tissue proximate a vagina of a patient. In other embodiments, the medical device 100 may be used to couple or attach different types of bodily implants into different locations within the body of the patient. In other embodiments, the medical device 100 may be used to couple one portion of bodily tissue to another portion of bodily tissue.

In some embodiments, the medical device 100 is configured to place tissue anchors or an anchoring device into a body of the patient to help secure a bodily implant within the body of the patient. In some embodiments, the medical device 100 is configured to grasp or retain a portion of the implant and/or a portion of the bodily tissue prior or during the placement of the tissue anchor.

The medical device 100 includes an elongate member 110, a first arm 130, a second arm 140, and a needle member 150. The elongate member 110 has a proximal end portion 112 and a distal end portion 114. The first arm 130 extends from the distal end portion 114 and is movably coupled to the elongate member 110. In some embodiments, the first arm 130 is rotatably coupled to the elongate member 110. In other embodiments, the first arm 130 is pivotally coupled to the elongate member 110. In yet other embodiments, another type of coupling is used to movably couple the first arm 130 to the elongate member 110. In some embodiments, the first arm 130 is monolithic or integrally formed with the elongate member 110 and is configured to flex or bend with respect to the elongate member 110.

In some embodiments, the first arm 130 includes a grip portion that is configured to grip or grasp a portion of a bodily implant and or bodily tissue. For example, in some embodiments the grip portion of the first arm 130 includes bumps, ridges, protrusions, or an otherwise non-planar portion or surface.

The second arm 140 extends from the distal end portion 114 of the elongate member 110 and is movably coupled to the elongate member 110. Accordingly, the second arm 140 is also configured to move with respect to the first arm 130. Similarly, the first arm 130 is configured to move with respect to the second arm 140. In some embodiments, the second arm 140 is rotatably coupled to the elongate member 110. In other embodiments, the second arm 140 is pivotally coupled to the elongate member 110. In yet other embodiments, another type of coupling is used to movably couple the second arm 140 to the elongate member 110. In some embodiments, the second arm 140 is monolithic or integrally formed with the elongate member 110 and is configured to flex or bend with respect to the elongate member 110.

In some embodiments, the second arm 140 includes a grip portion that is configured to grip or grasp a portion of a bodily implant and or bodily tissue. For example, in some embodiments the grip portion of the second arm 140 includes bumps, ridges, protrusions, or an otherwise non-planar portion or surface.

In the illustrated embodiment, the medical device 100 includes a first actuation member 160. The first actuation member 160 is operatively coupled to the first arm 130 and the second arm 140. For example, in some embodiments, the first actuation member 160 is operatively coupled to the first arm 130 and to the second arm 140 via a series of linkages or couplers. The first actuation member 160 is configured to move the first arm 130 and the second arm 140 with respect to the elongate member 110. For example, in some embodiments, the first actuation member 160 may be actuated, such as moved, pushed, pulled, or rotated, to move the first arm 130 and the second arm 140 towards or away from each other. In some embodiments, the first actuation member 160 is operatively coupled to only one of the first arm 130 and the second arm 140. In such embodiments, the first actuation member 160 may be actuated or activated to move only the first arm 130 or the second arm 140 with respect to the other arm and with respect to the elongate member 110.

The needle or needle member 150 is movably coupled to the elongate member 110. In some embodiments, the needle 150 is rotatably coupled to the elongate member 110. In some embodiments, the needle 150 is rotatably coupled about an axis that is perpendicular or substantially perpendicular to a longitudinal axis of the medical device 100. The needle member 150 is configured to lead or guide an anchor member into bodily tissue. In some embodiments, the needle 150 is curved or has a curved portion. In some embodiments, the needle 150 is configured to engage a tissue anchor 190 and guide or lead the tissue anchor 190 into bodily tissue of a patient to help secure an implant within the body of the patient. In some embodiments, the tissue anchor 190 extends through a portion of the bodily implant and through a portion of bodily tissue to help secure the implant within the body of the patient.

In some embodiments, the tissue anchor 190 is disposed within or housed within a lumen defined by the elongate member 110. For example, as will be described in detail below, in some embodiments, the tissue anchor 190 is disposed within or housed within the lumen of the elongate member 110 while the medical device 100 is inserted within the body of the patient. In some embodiments, more than one or a plurality of tissue anchors are disposed within or housed by the lumen of the elongate member 110.

In the illustrated embodiment, the medical device 100 includes a second actuation member 170. The second actuation member 170 is operatively coupled to the needle 150. The needle 150 is configured to move with respect to the elongate member 110 in response to the second actuation member 170 being activated or actuated. For example, in some embodiments, the second actuation member 170 may be pushed, pulled, twisted or otherwise moved to cause the needle 150 to move with respect to the elongate member 110. In some embodiments, the second actuation member 170 is operatively coupled to the needle 150 via linkages or other coupling members.

The medical device 100 and its components may be formed of any biocompatible material. For example, the medical device 100 and its components may be formed of a polymer material. In some embodiments, the needle 150 may be formed of a metal material, such as stainless steel. In some embodiments, the tissue anchor 190 may be formed of a permanent or a bioabsorbable material. In such embodiments, the tissue anchor 190 may be configured to dissolve or be absorbed by the body of the patient after being disposed within the body of the patient for a period of time.

In use, the medical device 100 may be inserted into the body of a patient. For example, the medical device 100 may be inserted into a pelvic region or another portion of the patient. In some embodiments, the medical device 100 is sized and shaped to fit within and be introduced into the body of the patient via a 10 mm-12 mm trocar. The medical device 100 may be positioned within the body such that the first arm 130 and the second arm 140 are disposed adjacent or are abutting a bodily implant and/or bodily tissue.

The first actuator 160 may then be actuated to cause the first arm 130 and the second arm to 140 to move with respect to the elongate member 110. Specifically, the first actuator 160 may be actuated to cause the first arm 130 and the second arm 140 to move towards each other to grip, grasp, or otherwise contain a portion of the bodily implant and/or the bodily tissue between the first arm 130 and the second arm 140.

The second actuator 170 may then be actuated to cause the needle 150 to rotate with respect to the elongate member 110. As the needle 150 rotates, the needle 150 is configured to drag, push, or otherwise advance and dispose a tissue anchor into the bodily implant and/or the bodily tissue. For example, in some embodiments, as the needle 150 rotates, the needle 150 drags, pushes, or otherwise advances and disposes a tissue anchor into the portion of the bodily implant and/or the bodily tissue that is disposed between or gripped by the first arm 130 and the second arm 140. In some embodiments, the needle 150 is configured to be actuated and to rotate less than an entire revolution. For example, in some embodiments, needle 150 may be configured to rotate in one direction to advance the tissue anchor into the bodily tissue of the patient and then rotate in an opposite direction to retract the needle from bodily tissue leaving the tissue anchor in place within the bodily tissue. In other embodiments, the needle 150 may be configured to rotate for an entire revolution (or rotate 360 degrees about an axis).

The first actuator 160 may then be released or actuated again to move the first arm 130 and the second arm 140 to release the bodily implant and/or the bodily tissue. This leaves the tissue anchor implanted within the body to help couple the implant to bodily tissue. The medical device 100 may then be removed from the body. In some embodiments, rather than being withdrawn or removed from the body of the patient, the medical device 100 may be relocated within the body and the process can be repeated to place a second tissue anchor within the body of the patient. For example, a series of tissue anchors may be placed to help retain the implant within the body of the patient.

Figure 2:
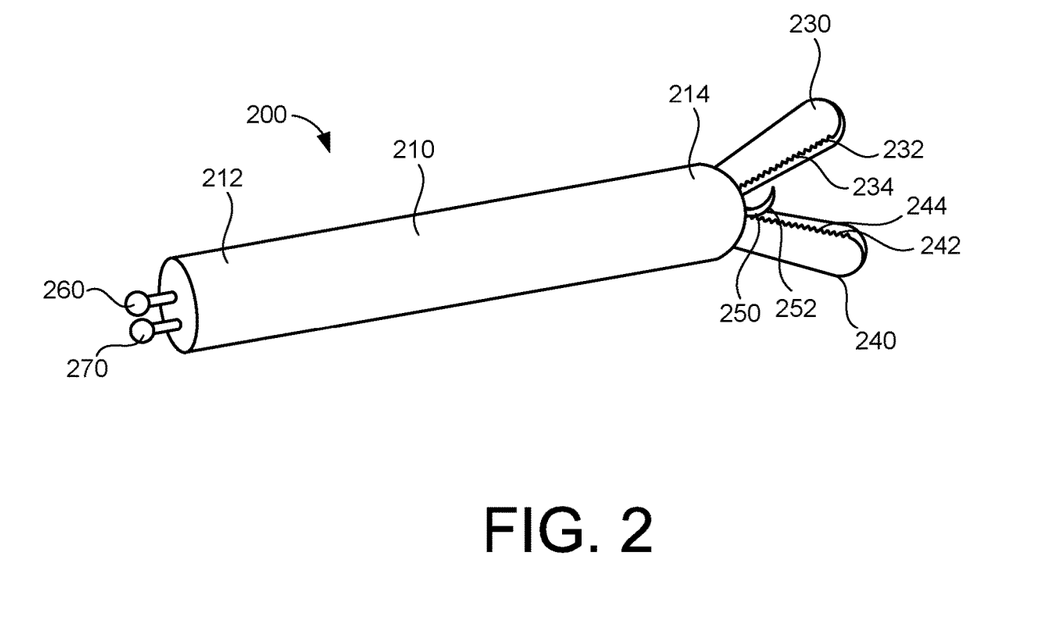
FIG. 2 is a perspective view of a medical device according to an embodiment.
Figure 3:
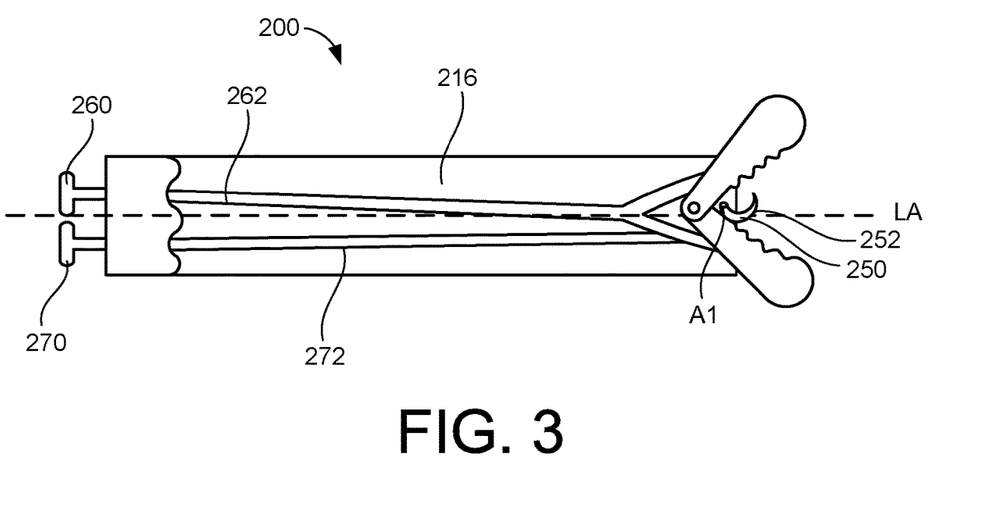
FIG. 3 is break-away view of the medical device of FIG. 2.

FIGS. 2 and 3 illustrate a medical device 200 according to an embodiment of the invention. The medical device 200 may be used to couple or attach a bodily implant within a body of a patient. For example, the medical device 200 may be used to couple or attach an implant within a pelvic region of a patient. For example, in some embodiments, the medical device 200 may be used in a sacrocolpopexy procedure to couple an implant to a vagina or tissue proximate a vagina of a patient. In other embodiments, the medical device 200 may be used to couple or attach different types of bodily implants into different locations within the body of the patient.

In some embodiments, the medical device 200 is configured to place tissue anchors or an anchoring device into a body of the patient to help secure a bodily implant within the body of the patient. In some embodiments, the medical device 200 is configured to grasp or retain a portion of the implant and/or a portion of the bodily tissue prior or during the placement of the tissue anchor.

The medical device 200 includes an elongate member 210, a first arm 230, a second arm 240, and a needle member 250. The elongate member 210 has a proximal end portion 212 and a distal end portion 214. The first arm 230 extends from the distal end portion 214 and is movably coupled to the elongate member 210. In the illustrated embodiment, the first arm 230 is rotatably coupled to the elongate member 210. In other embodiments, the first arm 230 is pivotally coupled to the elongate member 210. In yet other embodiments, another type of coupling is used to movably couple the first arm 230 to the elongate member 210. In some embodiments, the first arm 230 is monolithic or integrally formed with the elongate member 210 and is configured to flex or bend with respect to the elongate member 210.

In some embodiments, the first arm 230 includes a grip portion 232 that is configured to grip or grasp a portion of a bodily implant and or bodily tissue. For example, in the grip portion 232 of the first arm 230 includes bumps, ridges, protrusions, or an otherwise non-planar portion or surface 234.

The second arm 240 extends from the distal end portion 214 of the elongate member 210 and is movably coupled to the elongate member 210. Accordingly, the second arm 240 is also configured to move with respect to the first arm 230. Similarly, the first arm 230 is configured to move with respect to the second arm 240. In the illustrated embodiment, the second arm 240 is rotatably coupled to the elongate member 210. In other embodiments, the second arm 240 is pivotally coupled to the elongate member 210. In yet other embodiments, another type of coupling is used to movably couple the second arm 240 to the elongate member 210. In some embodiments, the second arm 240 is monolithic or integrally formed with the elongate member 210 and is configured to flex or bend with respect to the elongate member 210.

In some embodiments, the second arm 240 includes a grip portion 242 that is configured to grip or grasp a portion of a bodily implant and or bodily tissue. For example, in some embodiments the grip portion 242 of the second arm 240 includes bumps, ridges, protrusions, or an otherwise non-planar portion or surface 244.

In the illustrated embodiment, the medical device 200 includes a first actuation member 260. In the illustrated embodiment, the first actuation member 260 extends from the proximal end portion 212 of the elongate member 210. Accordingly, in the illustrated embodiment, the first actuation member 260 is accessible to a physician, doctor, or user when the distal end portion 214 of the elongate member 210 is disposed within a body of a patient. The first actuation member 260 is operatively coupled to the first arm 230 and the second arm 240. For example, in the illustrated embodiment, the first actuation member 260 is operatively coupled to the first arm 230 and to the second arm 240 via a series of linkages or couplers 262. In the illustrated embodiment, the series of linkages or couplers 262 are disposed within a lumen 216 defined by the elongate member 210. The first actuation member 260 is configured to move the first arm 230 and the second arm 240 with respect to the elongate member 210. For example, in some embodiments, the first actuation member 260 may be actuated, such as moved, pushed, pulled, or rotated, to move the first arm 230 and the second arm 240 towards or away from each other.

In some embodiments, the first actuation member 260 is operatively coupled to only one of the first arm 230 and the second arm 240. In such embodiments, the first actuation member 260 may be actuated or activated to move only the first arm 230 or the second arm 240 with respect to the other arm and with respect to the elongate member 210.

The needle or needle member 250 is movably coupled to the elongate member 210. In some embodiments, the needle 250 is rotatably coupled to the elongate member 210. In the illustrated embodiment, the needle 150 is rotatably coupled about an axis A1 (shown going into the page in FIG. 3) that is perpendicular or substantially perpendicular to a longitudinal axis LA of the medical device 200. The needle member 250 is configured to lead or guide an anchor member 290 into bodily tissue. In the illustrated embodiment, the needle 250 is curved or has a curved portion 252. In some embodiments, the needle 250 is configured to engage a tissue anchor 290 and guide or lead the tissue anchor 290 into bodily tissue of a patient to help secure an implant within the body of the patient. In some embodiments, the tissue anchor 290 extends through a portion of the bodily implant and through a portion of bodily tissue to help secure the implant within the body of the patient.

As best illustrated in FIGS. 4-7, in some embodiments, the tissue anchor 290 is disposed within or housed within a lumen 216 defined by the elongate member 210. For example, as will be described in detail below, in some embodiments, the tissue anchor 290 is disposed within or housed within the lumen of the elongate member 210 while the medical device 200 is inserted within the body of the patient. In some embodiments, more than one or a plurality of tissue anchors are disposed within or housed by the lumen of the elongate member 210.

In the illustrated embodiment, the medical device 200 includes a second actuation member 270. In the illustrated embodiment, the second actuation member 270 extends from the proximal end portion 212 of the elongate member 210. Accordingly, in the illustrated embodiment, the second actuation member 270 is accessible to a physician, doctor, or user when the distal end portion 214 of the elongate member 210 is disposed within a body of a patient. The second actuation member 270 is operatively coupled to the needle 250. The needle 250 is configured to move with respect to the elongate member 210 in response to the second actuation member 270 being activated or actuated. For example, in some embodiments, the second actuation member 270 may be pushed, pulled, twisted or otherwise moved to cause the needle 250 to move with respect to the elongate member 210. In the illustrated embodiment, the second actuation member 270 is operatively coupled to the needle 250 via linkages or other coupling members 272. In the illustrated embodiment, the linkages or other coupling members 272 are disposed within the lumen 216 defined by the elongate member 210.

The medical device 200 and its components may be formed of any biocompatible material. For example, the medical device 200 and its components may be formed of a polymer material. In some embodiments, the needle 250 may be formed of a metal material, such as stainless steel. In some embodiments, the tissue anchor 290 may be formed of a bioabsorbable material. In such embodiments, the tissue anchor 290 may be configured to dissolve or be absorbed by the body of the patient after being disposed within the body of the patient for a period of time.

Figure 4:
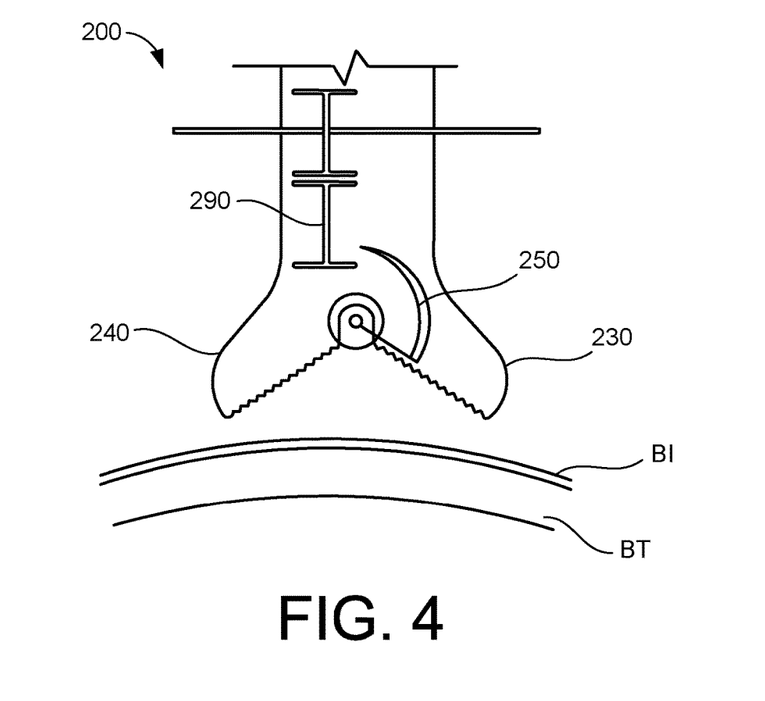
FIG. 4 is the medical device of FIG. 2 in a first position or configuration.

In use, the medical device 200 may be inserted into the body of a patient. For example, the medical device 200 may be inserted into a pelvic region or another portion of the body of the patient. In some embodiments, the medical device 200 is sized and shaped to fit within and be introduced into the body of the patient via a 10 mm-12 mm trocar. As illustrated in FIG. 4, the medical device 200 may be positioned within the body such that the first arm 230 and the second arm 240 are disposed adjacent or are abutting a bodily implant BI and/or bodily tissue BT.

Figure 5:
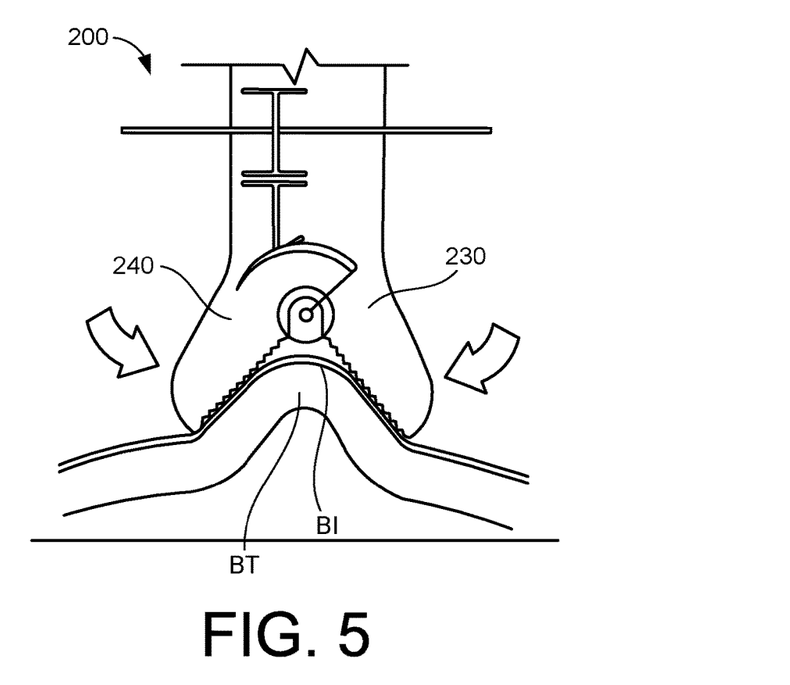
FIG. 5 is the medical device of FIG. 2 in a second position or configuration.

As best illustrated in FIG. 5, the first actuator 260 may then be actuated to cause the first arm 230 and the second arm to 240 to move with respect to the elongate member 210. Specifically, the first actuator 260 may be actuated to cause the first arm 230 and the second arm 240 to move towards each other (in the directions of arrows A and B, respectively) to grip, grasp, or otherwise contain a portion of the bodily implant BI and/or the bodily tissue BT between the first arm 230 and the second arm 240.

Figure 6:
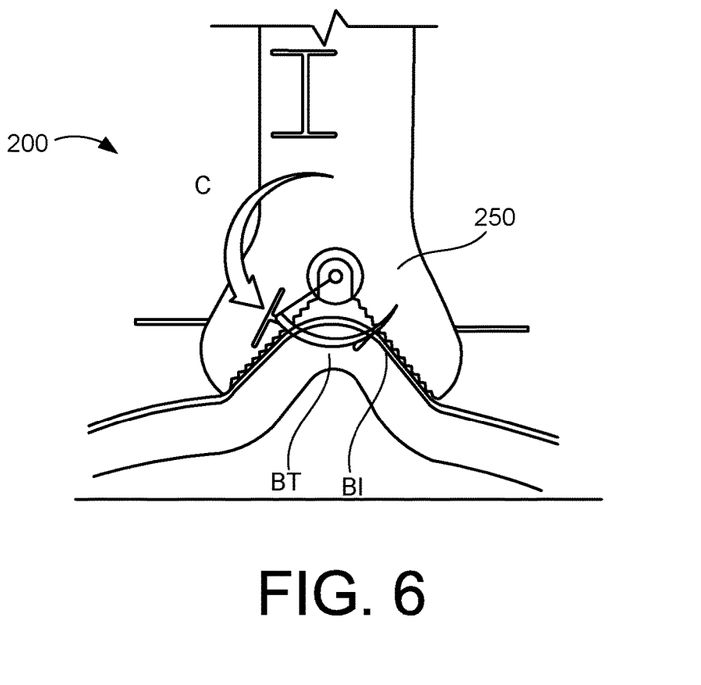
FIG. 6 is the medical device of FIG. 2 in a third position or configuration.

As best illustrated in FIG. 6, the second actuator 270 may then be actuated to cause the needle 250 to rotate with respect to the elongate member 210 in the direction of arrow C. As the needle 250 rotates, the needle 150 is configured to drag, push, or otherwise advance and dispose a tissue anchor into the bodily implant and/or the bodily tissue. For example, in some embodiments, as the needle 250 rotates, the needle 250 drags, pushes, or otherwise advances and disposes a tissue anchor 290 into the portion of the bodily implant BI and/or the bodily tissue BT that is disposed between or gripped by the first arm 230 and the second arm 240.

Figure 7:
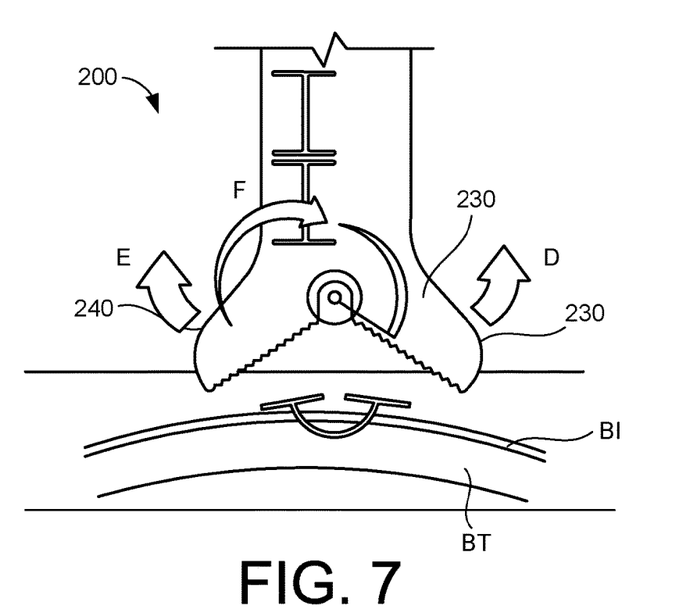
FIG. 7 is the medical device of FIG. 2 in a fourth position or configuration.

As best illustrated in FIG. 7, the needle 250 may be retracted (or rotated in the direction of arrow F. In some embodiments, the needle 250 may be retracted by actuating the second actuator 270 a second time. In other embodiments, the first actuation of the second actuator 270 causes the needle to rotate in the direction of arrow C and to retract (rotate in the direction of arrow F). Additionally, the first actuator 260 may then be released or actuated again to move the first arm 230 and the second arm 240 to release the bodily implant BI and/or the bodily tissue BT. This leaves the tissue anchor 290 implanted within the body to help couple the implant BI to bodily tissue BT. The medical device 200 may then be removed from the body. In some embodiments, rather than being withdrawn or removed from the body of the patient, the medical device 200 may be relocated within the body and the process can be repeated to place a second tissue anchor within the body of the patient. For example, a series of tissue anchors may be placed to help retain the implant within the body of the patient.

Figure 8:
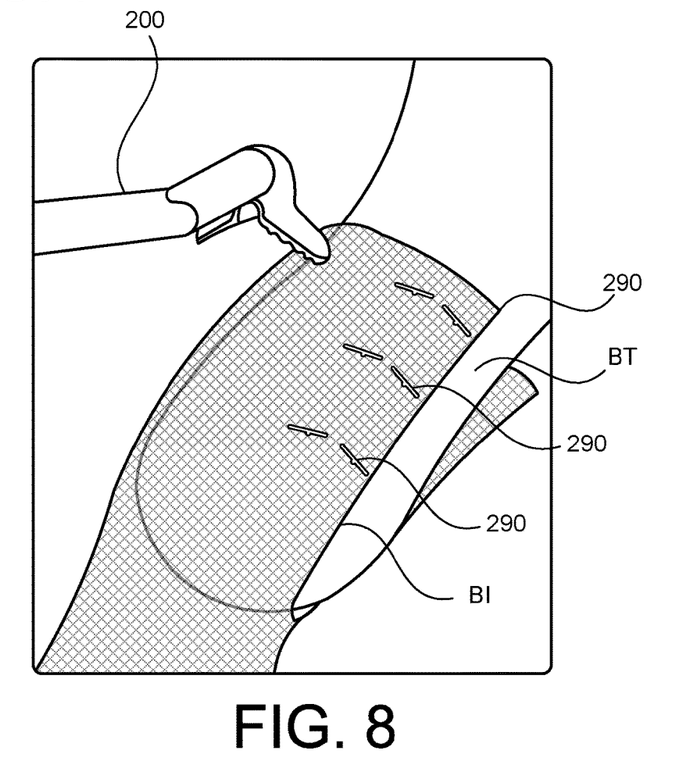
FIG. 8 is a schematic illustration of the medical device of FIG. 2 and an implant disposed within a body of a patient.

FIG. 8 is a schematic illustration of a bodily implant BI coupled to a portion of a body of a patient. In the illustrated embodiment, the bodily implant BI is a mesh material. In other embodiments, the bodily implant BI is of another type of material or form. In the illustrated embodiment, the bodily tissue BT is a vagina of a patient or bodily tissue disposed proximate a vagina of a patient. In other embodiments, the bodily tissue BT is another type of bodily tissue. In the illustrated embodiment, a plurality of tissue anchors 290 are used to help couple the bodily implant BI to the bodily tissue BT. As discussed above, the medical device 200 may be used to place any number of tissue anchors 290. For example, as best illustrated in FIGS. 4-7, a plurality of tissue anchors 290 may be loaded or placed within the lumen 216 of the elongate member 210. Each time the needle 250 rotates, the needle engages one of the tissue anchors 290 and pushes or delivers such tissue anchor 290 to the bodily implant and or bodily tissue.

Figure 9:
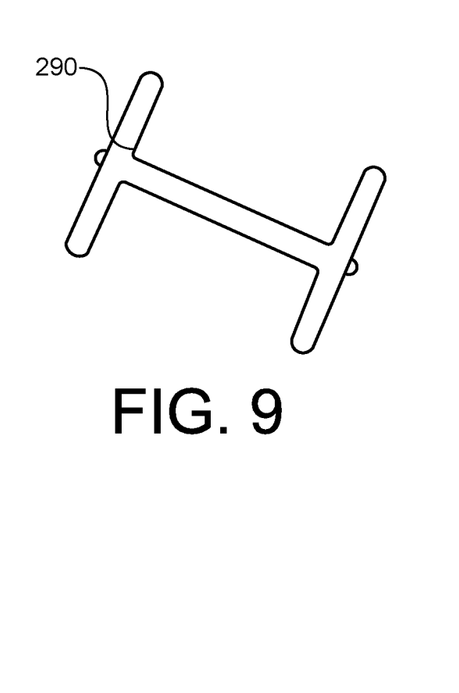
FIG. 9 is a top view of a tissue anchor according to an embodiment.
Figure 10:
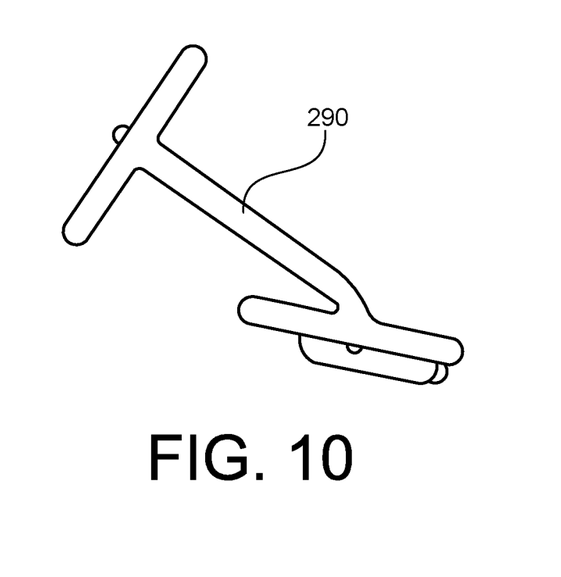
FIG. 10 is a top view of the tissue anchor of FIG. 9.

FIGS. 9 and 10 illustrate the tissue anchor 290. In the illustrated embodiment, the tissue anchor or tag member 290 is "H" shaped. As best illustrated in FIG. 8, the side portions of the "H" shaped tissue anchor 290 are disposed adjacent the bodily implant BI and the middle portion of the "H" shaped tissue anchor 290 extends through the bodily implant BI and the bodily tissue BT.

As illustrated in FIG. 10, in the illustrated embodiment, the tissue anchor 290 is formed of a flexible material. In some embodiments, the flexiblity of the tissue anchor 290 facilitates the insertion of the tissue anchor 290 into the bodily implant and the bodily tissue. Also as best illustrated in FIG. 10, in some embodiments, the tissue anchor 290 includes a coupling feature or portion 292. The coupling feature or portion 292 is configured to engage or be engaged by the needle 250 to facilitate the inserting of the tissue anchor within the body of the patient. For example, the coupling feature may define a slot, a cavity, or a shoulder that is configured to contact or engage the needle 250 to facilitate the movement of the tissue anchor into the bodily tissue by the needle 250.

Figure 11:
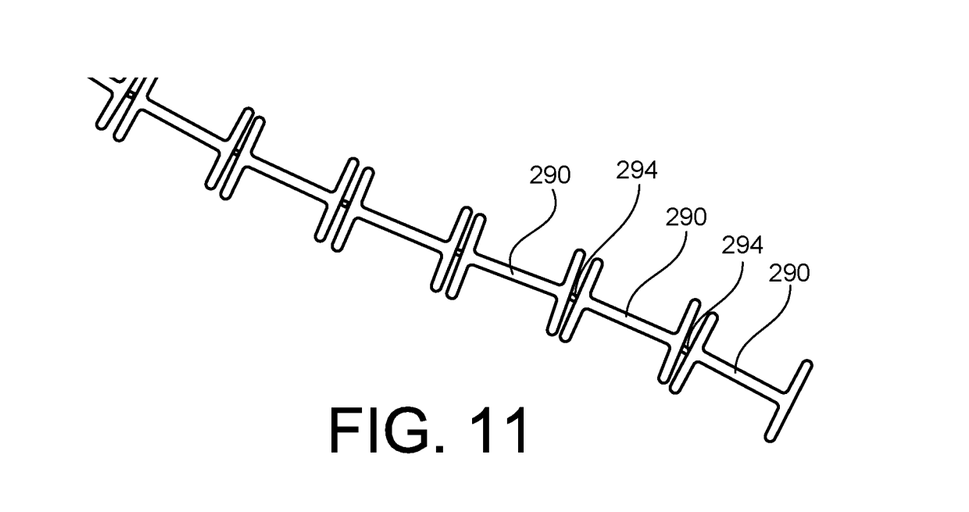
FIG. 11 is a top view of a series of tissue anchors according to an embodiment.

FIG. 11 illustrates a series or a plurality of tissue anchors 290. The tissue anchors 290 are coupled together via a connection member 294. The connection member 294 is configured to break such that the individual tissue anchors 290 are released in response to the needle 250 moving or pushing the specific tissue anchor out of the lumen 216 and into the bodily tissue of the patient. Accordingly, in such embodiments, the series of tissue anchors may be loaded into the medical device 200 and each one individually inserted into the bodily tissue of the patient (for example, at different locations within the bodily tissue).

Figure 12:
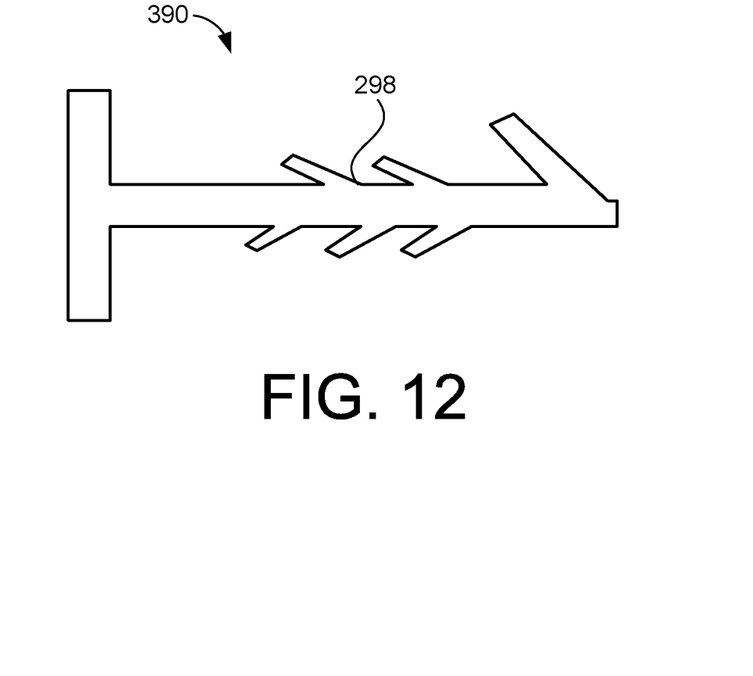
FIG. 12 is a top view of a tissue anchor according to an embodiment.

FIG. 12 illustrated another tissue anchor 390. The tissue anchor 390 includes a set or series of barbs or projections 398. In some embodiments, the series of barbs or projections 398 are configured to help retain the tissue anchor within the bodily tissue of the patient.

Figure 13:
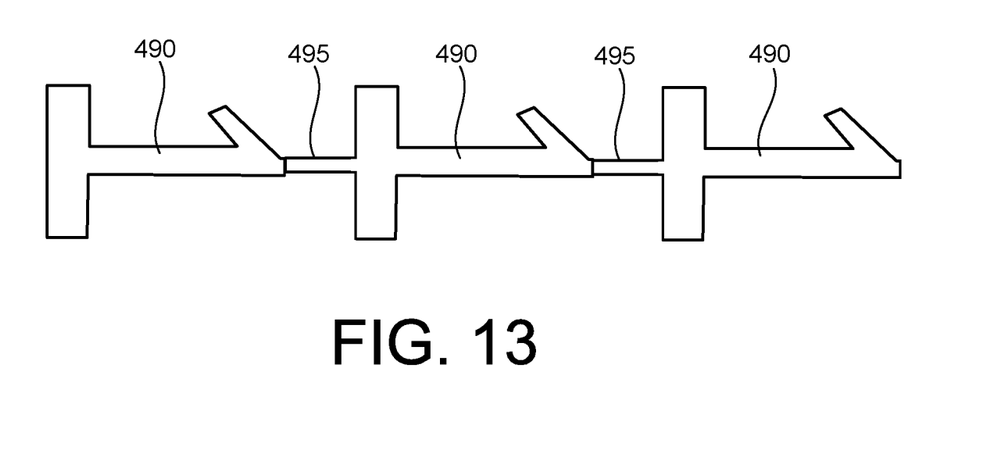
FIG. 13 is a top view of a series of tissue anchors according to an embodiment.

FIG. 13 illustrates a set or series of tissue anchors 490. The tissue anchors 490 are coupled together via a connection member 494. The connection member 494 is configured to break such that the individual tissue anchors 490 are released in response to the needle 250 moving or pushing the specific tissue anchor out of the lumen 216 and into the bodily tissue of the patient. Accordingly, in such embodiments, the series of tissue anchors may be loaded into the medical device 200 and each one individually inserted into the bodily tissue of the patient (for example, at different locations within the bodily tissue).

While tissue anchor of various shapes have been illustrated, the tissue anchor may be of any shape or size.

Figure 14:
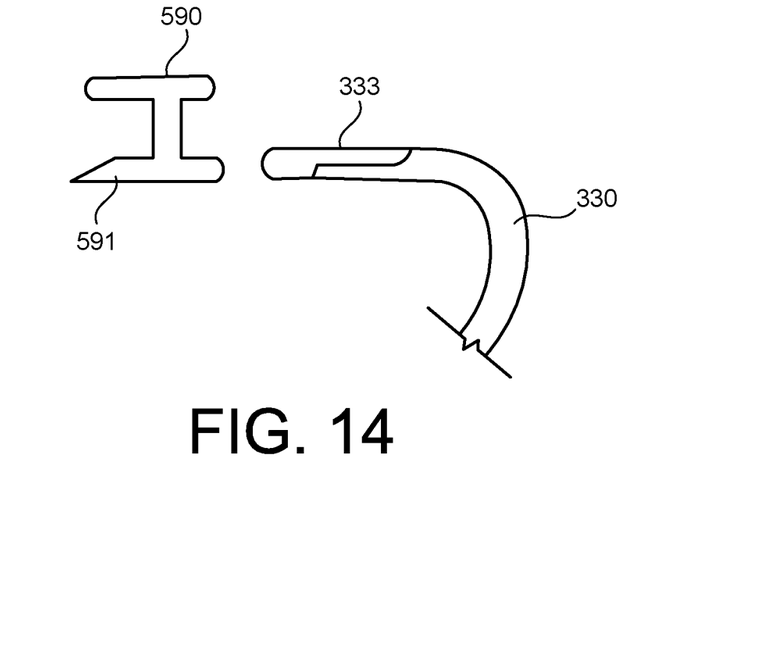
FIGS. 14 and 15 are side views of a needle and a tissue anchor according to an embodiment.
Figure 15:
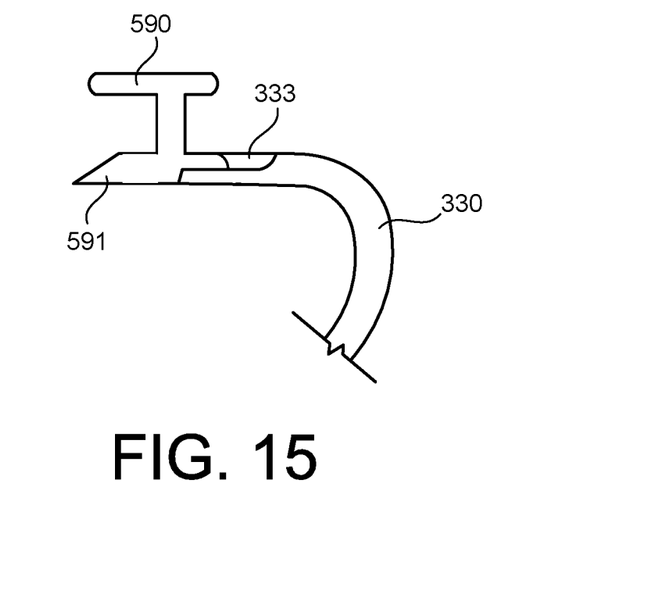

FIGS. 14 and 15 illustrate a needle 330 and a tissue anchor 590 according to an embodiment. The needle 330 includes a slot or otherwise defines a cavity 333. As best illustrated in FIG. 15, the slot or cavity 333 is configured to receive a portion of the tissue anchor 590. Accordingly, the needle 330 can move or rotate proximate or adjacent the tissue anchor 590. As the needle 330 moves, the slot or cavity can receive a portion of the tissue anchor 590 to engage or couple the tissue anchor 590 to the needle 330. In the illustrate embodiment, the tissue anchor 590 includes sharp or pointed end portion 591. The sharp or pointed end portion 591 is configured to puncture or pierce bodily tissue. Accordingly, in this embodiment, as the needle 330 is advanced to move the tissue anchor into place within the body of the patient, the sharp or pointed end portion 591 can pierce the bodily tissue and lead the tissue anchor 590 through the bodily tissue. In the illustrated embodiment, the tissue anchor 590 is configured to disengage or become uncoupled from the needle 330 when the needle 330 is retraced from the bodily tissue.

Figure 16:
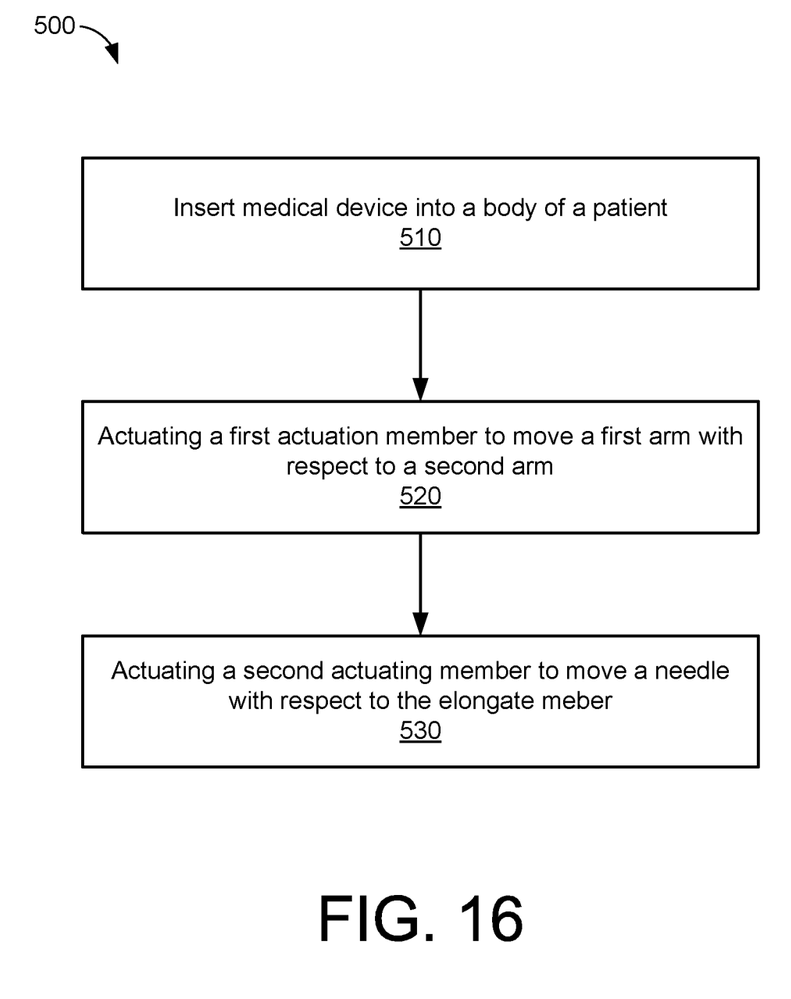
FIG. 16 is a flow chart of a method according to an embodiment.

FIG. 16 is a flow chart for a method 500 according to an embodiment. The method may be used to insert or couple a bodily implant within a body of a patent. At 510, a medical device is inserted into a body of a patient. The device may be inserted into any portion of the body. In some embodiments, the device is inserted into a pelvic region of the patient. In some embodiments, the medical device is inserted into the body such that the medical device or a portion of the medical device is disposed adjacent or abutting bodily tissue and or a bodily implant.

At 520, a first actuation member of the medical device is actuated. The first actuation member may be actuated by pulling, pushing, or otherwise moving or engaging the first actuation member. Actuation of the first actuation member causes a first arm and a second arm of the medical device to move towards each other. In some embodiments, the arms move towards each other and grip, grasp, pinch, or otherwise retain bodily tissue and/or a bodily implant between the arms.

At 530, a second actuation member is actuated. The second actuation member may be actuated by pulling, pushing, rotating, or otherwise moving or engaging the second actuation member. Actuation of the second actuation member causes a needle of the medical device to move or rotate with respect to an elongate member of the medical device. The movement of the needle causes a tissue anchor to be inserted into the bodily tissue and/or the bodily implant. In some embodiments, the tissue anchor is inserted into the bodily tissue and/or the bodily implant that is disposed between the first arm and the second arm.

The first arm and the second arm may then be moved back to their original position (so as to not be gripping or grasping bodily tissue). This may be done by releasing the first actuation member or by actuating the first actuation member for a second time. In some embodiments, the medical device is then removed from the body of the patient. In other embodiments, the medical device is moved to another location within the body and the process is repeated to place another tissue anchor within the body of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
    an elongate member having a proximal end portion and a distal end portion, the elongate member defining a longitudinal axis;
    a first tissue anchor and a second tissue anchor disposed in the elongate member;
    a first arm extending from the elongate member;
    a second arm extending from the elongate member, the first arm and the second arm being configured to rotate about an axis that is located along the longitudinal axis of the elongate member and extends substantially perpendicular to the longitudinal axis of the elongate member; and
    a needle rotatably coupled to the elongate member, the needle being configured to rotate about an axis that is located along the longitudinal axis of the elongate member and extends substantially perpendicular to the longitudinal axis of the elongate member, the needle configured to engage the first tissue anchor and guide the first tissue anchor into a tissue of a patient, the first tissue anchor being removably coupled to the second tissue anchor via a connection member.

2. The medical device of claim 1, further comprising:
    an actuation mechanism configured to cause the second arm to move with respect to the first arm in response to being actuated.

3. The medical device of claim 1, further comprising:
    an actuation mechanism configured to cause the needle to move with respect to the elongate member in response to being actuated.

4. The medical device of claim 1, further comprising:
    a first actuation mechanism configured to cause the second arm to move with respect to the first arm in response to being actuated; and
    a second actuation mechanism configured to cause the needle to rotate with respect to the elongate member in response to being actuated.

5. The medical device of claim 1, wherein the elongate member defines a lumen, the lumen being configured to retain the plurality of tissue anchors.

6. The medical device of claim 1, wherein the needle includes a curved portion.

7. The medical device of claim 1, wherein the first arm includes a non-planar surface, the non-planar surface being configured to contact at least one of a bodily implant and bodily tissue of a patient.

8. The medical device of claim 1, wherein the first arm includes a non-planar surface, the non-planar surface of the first arm being configured to contact at least one of a bodily implant and bodily tissue of a patient, the second arm includes a non-planar surface, the non-planar surface of the second arm being configured to contact at least one of a bodily implant and bodily tissue of the patient.

9. The medical device of claim 1, wherein the first tissue anchor includes a coupling portion that is configured to engage with the needle.

10. The medical device of claim 9, wherein the second tissue anchor includes a coupling portion that is configured to engage with the needle.

11. A medical device, comprising:
    an elongate member having a proximal end portion and a distal end portion, the elongate member defining a longitudinal axis;
    a plurality of tissue anchors disposed in the elongate member;
    a first arm extending from the elongate member, the first arm being configured to move with respect to the elongate member;
    a second arm extending from the elongate member, the second arm being configured to move with respect to the elongate member;
    a needle rotatably coupled to the elongate member, the needle being configured to engage the plurality of tissue anchors disposed in the elongate member and guide one tissue anchor of the plurality of tissue anchors into a tissue of a patient;
    a first actuation member operatively coupled to the first arm and the second arm via a connecting member, the connection member of the first actuation member extending substantially parallel along the longitudinal axis; and
    a second actuation member operatively coupled to the needle via a connecting member, the connection member of the second actuation member extending substantially parallel along the longitudinal axis.

12. The medical device of claim 11, wherein the first arm is pivotally coupled to the elongate member.

13. The medical device of claim 11, wherein the first arm is rotatably coupled to the elongate member.

14. The medical device of claim 11, further comprising:
an actuation mechanism configured to cause the second arm to move with respect to the first arm in response to being actuated.

15. The medical device of claim 11, further comprising:
an actuation mechanism configured to cause the needle to rotate with respect to the elongate member in response to being actuated.

16. The medical device of claim 11, further comprising:
a first actuation mechanism configured to cause the second arm to move with respect to the first arm in response to being actuated; and
a second actuation mechanism configured to cause the needle to rotate with respect to the elongate member in response to being actuated.

17. The medical device of claim 11, wherein the elongate member defines a lumen, the lumen being configured to retain the plurality of tissue anchors.

18. A method, comprising:
inserting a medical device into a body of a patient, the medical device including an elongate member having a proximal end portion and a distal end portion, the elongate member defining a longitudinal axis, a first tissue anchor and a second tissue anchor disposed in the elongate member, a first arm extending from the elongate member, a second arm extending from the elongate member, the first arm and the second arm being configured rotate about an axis that is located along the longitudinal axis of the elongate member and extends substantially perpendicular to the longitudinal axis of the elongate member, and a needle coupled to the elongate member, the needle being configured to move with respect to the elongate member and to engage the first tissue anchor and guide the first tissue anchor into the body of the patient, the first tissue anchor being removably coupled to the second tissue anchor via a connection member;
actuating a first actuation member to move the second arm with respect to the first arm so as to dispose a portion of a bodily implant and bodily tissue of a patient between the first arm and the second arm; and
actuating a second actuation member to rotate the needle about an axis that is located along the longitudinal axis of the elongate member and extends substantially perpendicular to the longitudinal axis of the elongate member to insert the first tissue anchor into the bodily implant and the bodily tissue.

19. The method of claim 18, wherein the elongate member defines a lumen, the lumen retains the plurality of tissue anchors during the inserting.

20. The method of claim 18, wherein the needle includes a curved portion and is configured to rotate with respect to the elongate member in response to the actuating of the second actuation member.

* * * * *